(12) United States Patent
Schwarz (10) Patent No.: US 6,433,136 B1
(45) Date of Patent: *Aug. 13, 2002

(54) CELL DENSITY SIGNAL PROTEIN SUITABLE FOR TREATMENT OF CONNECTIVE TISSUE INJURIES AND DEFECTS

(75) Inventor: Richard I. Schwarz, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/215,184

(22) Filed: Dec. 17, 1998

Related U.S. Application Data (63) Continuation-in-part of application No. 09/061,717, filed on Apr. 17, 1998, now Pat. No. 6,245,899, which is a division of application No. 08/445,367, filed on May 19, 1995, now Pat. No. 5,741,895, which is a continuation of application No. 08/049,481, filed on Apr. 19, 1993, now abandoned, which is a continuation-in-part of application No. 07/570,422, filed on Aug. 21, 1990, now abandoned.

(60) Provisional application No. 60/087,882, filed on Jun. 3, 1998.

(51) Int. Cl.$^7$ ................................................. C07K 7/00

(52) U.S. Cl. ....................... 530/324; 530/327; 530/350; 530/351

(58) Field of Search ............................... 530/350, 840, 530/351, 398, 356, 327, 324; 435/69.1

(56) References Cited

U.S. PATENT DOCUMENTS 5,908,763 A * 6/1999 Clark et al.

OTHER PUBLICATIONS

Burgess et al. J of Cell Biol. 111, 2129–2138, 1990.*
Lazar et al. Mol. Cell Biol. 8: 1247–1252, 1988.*
Tao et al., J. Immunol. 143, 2595–2601, 1989.*
WO9719172, Genbank AC W18349, May 1997.*
Lucy B. Rowe, et al., Role of Procollagen mRNA Levels in Controlling the Rate of Procollagen Synthesis, *Molecular and Cellular Biology*, 3/2:241–249 (Feb. 1983).
Richard I. Schwarz, Cell–to–Cell Signaling in the Regulation of Procollagen Expression in Primary Avian Tendon Cells, *In Vitro Cell. Div. Biol.*, 28A:698–706 (Sep. 1991).
Julie R. Zayas, et al., Evidence Supporting the Role of a Proteinaceous, Loosely Bound Extracellular Molecule in the Cell Density Signaling Between Tendon Cells, *In Vitro Cell. Div. Biol.*, 28A:745–754 (Nov.–Dec. 1992).
Richard I. Schwarz, et al., Dependence of the Differentiated State on the Cellular Environment: Modulation of Collagen Synthesis in Tendon Cells, *Proc. Natl. Acad. Sci. USA*, 74/10:4453–4457 (Oct. 1997).
Richard I. Schwarz, Modeling Tendon Morphogenesis In Vivo Based on Cell Density Signaling in Cell Culture, *J. Math. Biol.*, 35:97–113 (1996).

* cited by examiner

*Primary Examiner*—Sheela Huff
(74) *Attorney, Agent, or Firm*—Hana Verny (57) ABSTRACT

Identification, isolation and partial sequencing of a cell density protein produced by fibroblastic cells. The cell density signal protein comprising a 14 amino acid peptide or a fragment, variant, mutant or analog thereof, the deduced cDNA sequence from the 14 amino acid peptide, a recombinant protein, protein and peptide-specific antibodies, and the use of the peptide and peptide-specific antibodies as therapeutic agents for regulation of cell differentiation and proliferation. A method for treatment and repair of connective tissue and tendon injuries, collagen deficiency, and connective tissue defects.

7 Claims, 5 Drawing Sheets

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: cell density
      signal  molecule

<400> SEQUENCE: 1

Glu Pro Leu Ala Val Val Asp Leu Thr Glu Lys Thr Ile Ser
 1               5                  10
```

CELL DENSITY SIGNAL PROTEIN SUITABLE FOR TREATMENT OF CONNECTIVE TISSUE INJURIES AND DEFECTS

This application is partly based on provisional application Ser. No. 60/087,882, filed on Jun. 3, 1998 and is a continuation-in part of application Ser. No. 09/061,717, filed on Apr. 17, 1998, now U.S. Pat. No. 6,245,899 which is a divisional of application Ser. No 08/445,367, filed on May 19, 1995, issued as U.S. Pat. No. 5,741,895 on Apr. 21, 1998, which is a continuation of application Ser. No. 08/049,481, filed on Apr. 19, 1993, now abandoned, which is a continuation-in-part of application Ser. No. 07/570,422, filed on Aug. 21, 1990 now abandoned.

REFERENCE TO GOVERNMENT INTEREST

This invention was made in the course of contract DE-AC03-76SF0098 between the United States Department of Energy and the University of California for the operation of Lawrence Berkeley Laboratory. The United States Government has certain rights to this invention.

BACKGROUND OF THE INVENTION

Field of the Invention

This invention concerns identification, isolation and partial sequencing of a cell density signaling protein produced by fibroblastic cells. In particular, the invention concerns the cell density signaling protein comprising a 14 amino acid N-terminal peptide or a fragment, variant, mutant or analog thereof, the deduced cDNA sequence from the 14 amino. acid peptide, a recombinant protein, protein and peptide-specific antibodies, and the use of the peptide and peptide-specific antibodies as therapeutic agents for regulation of cell differentiation and proliferation. The invention further concerns a method for treatment and repair of connective tissue and tendon injuries, collagen deficiency, connective tissue defects and reversal of connective tissue aging.

BACKGROUND AND RELATED DISCLOSURES

The level of collagen formation depends on the level of procollagen expression, a differentiated function of most fibroblastic cells in culture. The procollagen expression is under the regulation of several environmental factors, one of which is cell density.

Beginning in the early 1960's investigators observed that an enhancement of collagen production was dependent upon an increase in cell density. However, despite its long history, little is known about the signaling mechanism that allows the cell to recognize the presence of its neighbors and translate this information into increased collagen synthesis.

Most cell types which naturally express procollagen in vivo lose this ability over time when placed in cell cultures. However, primary avian tendon (PAT) cells, when grown in a cell culture environment that is permissive for high procollagen expression, retain the potential for high levels of collagen expression, and, in this regard, demonstrate a dependency of the collagen expression on the density of the cell culture. PAT cells increase their production of procollagen in direct relation to cell density from less than 10% to about 50% of total protein synthesis, as described in *Proc. Nat. Acad. Sci.*, 74:4453–4457 (1977).

The proliferative capacity of cells in culture is also affected by cell density. However, a definitive correlation has been difficult to obtain because cell proliferation is affected by many other cell culture parameters, only one of which is cell density. For instance, it is difficult to distinguish the effect of density per se from the possibility that cell density changes are a subset of the nutritional needs of the cell. Cell density effect may also be affected by decreased access to growth factors as cells lay down an extracellular matrix. This is supported by findings that changing the medium and even just shaking the medium above the cells is sufficient to stimulate cell division (*Cell* 3:207–215 (1974)).

Cell contact may also play a role in this event, as demonstrated by the fact that membrane components shed into the medium appear to inhibit cell proliferation. (*Exp. Cell Research*, 133:415–419 (1991))

Consequently, the relationship between cell density on the one hand and cell proliferation and the expression of differentiated function such as procollagen gene expression in the case of PAT cells, on the other hand, has been a complex problem for which it has been particularly difficult to design definitive experiments. Despite these complications, several publications describe proteins which are reported to affect density dependent cell growth. For example, a 40–45 kD density-dependent growth inhibitor, isolated from mouse 3T3 cells has been described in *J. Cell. Physiol.*, 119:101–106 (1984); *J. Cell. Physiol.*, 123:139–143 (1985); and *J. Cell. Physiol.*, 130:416–419 (1987).

*Cancer Res.*, 38:635–643 (1978), and *J. Invest. Dermatol,*. 87:309–312 (1986) disclose a contact inhibitory factor, isolated from hamster melanocytic cells, which restores density-dependent growth to melanoma cells. *GANN Monograph on Cancer Res.*, 25:29–39 (1980) discloses a low molecular weight (6–8 kD) growth inhibitory factor from the cell surface of chick embryo fibroblasts.

However, despite the extensive research in the cell density and collagen expression area, the regulatory mechanism and regulatory compounds for collagen were never discovered.

In view of serious consequences of joints and tendon injuries which are connected with and are dependent on collagen formation, it would be desirable to have available means to regulate the collagen synthesis or procollagen expression and to identify their regulators.

It is, therefore, a primary objective of the current invention to isolate, identify, purify and synthesize a protein which acts as a regulator of collagen production.

All patents, patent applications and publication referred to in the specification are hereby incorporated by reference.

SUMMARY OF THE INVENTION

One aspect of the current invention is a protein produced by the fibroblastic cells acting as a cell density signal molecule able to regulate a cell differentiation and proliferation.

Another aspect of the current invention is an isolated, purified, naturally occurring or recombinantly prepared cell density signal (CDS) protein comprising a 14 amino acid peptide as its N-terminus portion, or any fragment, variant, mutant or analog of said peptide which does not change the functional characteristics of the cell density signal protein and retains the protein's biological activity.

Still another aspect of the current invention is a peptide having an amino acid sequence Glu-Pro-Leu-Ala-Val-Val-Asp-Leu-Thr-Glu-Lys-Thr-Ile-Ser (SEQ ID NO:1) or any fragment, variant, mutant or analog thereof functioning in the same way as the whole 14 amino acid peptide wherein said peptide, fragment, variant, mutant or analog are located at N-terminus of CDS protein.

Still another aspect of the current invention is a deduced cDNA sequence encoding a peptide having an amino acid sequence Glu-Pro-Leu-Ala-Val-Val-Asp-Leu-Thr-Glu-Lys-Thr-Ile-Ser (SEQ ID NO:1) or any fragment, variant, mutant, analog thereof which expresses a peptide fragment, variant, mutant or analog functioning in the same way as the whole peptide of 14 amino acid sequence.

Still yet another aspect of the current invention is a recombinant peptide having an amino acid sequence Glu-Pro-Leu-Ala-Val-Val-Asp-Leu-Thr-Glu-Lys-Thr-Ile-Ser (SEQ ID NO:1) or any fragment, variant, mutant or analog thereof functioning in the same way as the whole 14 amino acid peptide.

Still yet another aspect of the current invention are antibodies which are specific for the cell density signal protein, 14 amino acid peptide or for any biologically active fragment, variant, mutant or analog thereof.

Another aspect of the current invention is a specific antibody recognizing a CDS protein comprising a peptide having an amino acid sequence Glu-Pro-Leu-Ala-Val-Val-Asp-Leu-Thr-Glu-Lys-Thr-Ile-Ser (SEQ ID NO:1) or a fragment, variant, mutant or analog thereof.

Still another aspect of the current invention are methods of obtaining, isolating, synthesizing and purifying cell density signal protein or 14 amino acid peptide.

Still yet another aspect of the current invention is a method for treatment of injuries and defects of connective tissue, joints and tendons.

Still another aspect of the current invention is a method for treatment of tendon and ligaments injuries and defects, said method comprising administering to a subject in need thereof a therapeutically effective amount of a protein comprising a peptide of the invention having an amino acid sequence SEQ ID NO:1, or a fragment, variant, mutant or analog thereof alone or in admixture with pharmaceutically acceptable excipients.

BRIEF DESCRIPTION OF DRAWINGS

FIG. 2 shows in situ hybridization with a probe to procollagen mRNA in cells grown as an island in the middle of the disk. A high cell density (FIG. 2A); moderate density (FIG. 2C); low density (FIG. 2D); section of the island (FIG. 2B).

FIG. 3 illustrates properties of shaken conditioned medium on PAT cell growth.

FIG. 6 shows fractions of the unbound flow-through (FIG. 6A) and bound fractions (FIG. 6B) of the active protein separated on a reducing SDS PAGE.

DEFINITIONS

As used herein:

"CDS", "cell density signal molecule" or "cell density signal protein" means a protein comprising as its N-terminus a 14 amino acid peptide having an amino acid sequence Glu-Pro-Leu-Ala-Val-Val-Asp-Leu-Thr-Glu-Lys-Thr-Ile-Ser (SEQ ID NO: 1) or any fragment, variant, mutant or analog thereof functioning in the same way as the whole 14 amino acid peptide.

"EPLAVVDLTEKTIS" or "SEQ ID NO:1" means amino acid sequence Glu-Pro-Leu-Ala-Val-Val-Asp-Leu-Thr-Glu-Lys-Thr-Ile-Ser of the 14 amino acid peptide.

"Autogenic" means derived either from the same individual, from a cell culture derived from an individual, from multiple inbred individuals, or from cultures derived from multiple inbred individuals.

"Biologically active" means isolated, purified, naturally occurring or recombinantly prepared cell density signal peptide and any fragment, variant, mutant or analog thereof which retains biological characteristics of the cell density signal peptide in regulating cell differentiation and proliferation.

"Differentiated gene expression" or "the expression of differentiated function" or "differentiated function" means the transcription and translation of structural genes other than those associated with cellular division or viability. The polypeptides so expressed are those which characterize differentiated cells as opposed to immature or "blastic" cells.

"Extracellular matrix" or "ECM" means a network of macromolecules upon, or within, which cells subsist. The extracellular matrix is comprised of, but not limited to, collagen, limonene, fibronectin, glycosaminoglycans, proteoglycans, etc. In vivo, the ECM is produced by cells within the matrix or by peripheral cells, and is an integral part of stromal tissue. In culture, many cell types require the ECM for the expression of proper differentiated characteristics.

"Functionally homologous" means proteinaceous molecules which are functionally homologous, that is those which exhibit the same functional characteristics. For example, an enzyme from one species is functionally homologous with an enzyme from another species if they both catalyze the same reaction. The proteinaceous cell density signal molecules from different species are functionally homologous if they exhibit the same amphipathic regulation of growth and differentiated function for the corresponding autogenic fibroblastic cells in culture. In the subject invention, for example, functionally homologous means that the chicken tendons and human tendons were found to be very similar which agrees with prior findings that the collagen structure in both species is also very similar (*Biochemistry*, 22:1139 (1983)). Consequently, the chicken cell density signal molecule isolated from chicken cells is expected to be functionally homologous to the cell density signal molecule isolated from human cells.

A "peptide" or "protein" includes the naturally occurring peptide or protein and all fragments, deletions, additions, substitutions, mutations and modifications of the natural protein or within the peptide portion of the protein which retain the biological activities and functional characteristics of the naturally occurring protein. A glycosylated or otherwise modified protein is included within the scope of the term as used herein and may also be more specifically referred to as a proteoglycan, glycopeptide or glycoprotein. A proteinaceous molecule of the invention comprises a peptide.

"Primary culture of cells" means a culture of cells which is derived from in vivo tissue and not passaged. Primary cultures can be distinguished from cell strains and established cultures principally by the retention of a karyotype which is substantially identical to the karyotype found in the tissue from which the culture was derived, and by the cellular responses to manipulations of the environment, that is the responses which are substantially similar to the in vivo response.

"Basal growth medium" or "unsupplemented basal growth medium", unless otherwise specifically described, is a defined cell culture growth medium without the addition of serum or other growth supplements.

DETAILED DESCRIPTION OF THE INVENTION

The current invention discloses a proteinaceous cell density signal molecule, exhibiting a molecular weight of at least about 16 kD to about 35 kD. The invention further discloses isolated purified cell density signal (CDS) proteins having an apparent molecular weight when analyzed on SDS polyacrylamide gel electrophoresis (SDS-PAGE) of about 16 kD and about 20 kD, and identifies the specific 14 amino acids comprised therein. The sequenced peptide, or a biologically active fragment, variant, mutant or analog thereof comprises the N-terminal portion of the cell density signal protein. The CDS protein associates with the extracellular matrix of the primary avian tendon (PAT) cells in culture, transiently stimulates the proliferation of these cells and subsequently stimulates procollagen gene expression. The invention also discloses a method for treatment and correction of connective tissue and tendon defects and injuries.

This invention additionally concerns a peptide, fragment, variant, mutant or analog thereof which is localized at the N-terminus of a cell density signal protein (CDS) for regulation of a connective tissue and cells proliferation and differentiation and for expression of procollagen. The peptide was isolated, purified, sequenced and the amino acid sequence was determined to be Glu-Pro-Leu-Ala-Val-Val-Asp-Leu-Thr-Glu-Lys-Thr-Ile-Ser, designated as SEQ ID NO:1.

The invention further concerns a deduced cDNA nucleotide sequence encoding said peptide, or any fragment, variant, mutant or analog thereof having the same function within the CDS protein as the whole 14 amino acid peptide, and a corresponding recombinant peptide, a CDS protein or peptide specific antibody useful for treatment of connective tissue injuries, a method for preparation of a recombinant peptide and a method for treatment of tendon or other connective tissue injuries and diseases by providing a subject in need thereof a therapeutically effective amount of the recombinantly prepared cell density signal protein comprising a 14 amino acid peptide.

I. Cell Density Signal Proteins

A proteinaceous cell density signal (CDS) molecule is a protein useful for regulation of procollagen expression and proliferation and differentiation of connective tissue and cells, such as tendons and ligaments.

The CDS molecule is a protein which contain at least a 5 amino acid portion of the 14 amino acid sequence identified as SEQ ID NO:1 localized at its N-terminus, or any other fragment larger than 5 amino acids, or any mutant larger than 5 amino acid, or any variant larger than 5 amino acids or any analog larger than 5 amino acid of the sequence SEQ ID NO:1 which asserts the same biological effect as the whole CDS molecule.

During the development of this invention, the native CDS protein has been isolated from the chicken tendons, tested for its activity, purified and partially sequenced at N-terminus. The unpurified protein isolated from the primary avian tendon has originally been found to have a molecular weight between about 25 up to about 100 kD on size exclusion chromatography. The isolated, purified and sequenced CDS peptide was found to contain two biologically active fractions containing 150–200 amino acids having an apparent molecular weight 16 and 20 kD on SDS-PAGE. The purified peptide has a following 14 amino acids sequence Glu-Pro-Leu-Ala-Val-Val-Asp-Leu-Thr-Glu-Lys-Thr-Ile-Ser, designated as SEQ ID NO:1.

The CDS protein was found to be capable of stimulating the proliferation of tendon cells in culture and promoting differentiated gene expression. The CDS protein is thus the cells self-regulator or regulator of the cell's proliferation and expression of differentiated function.

The CDS protein is secreted by fibroblastic cells, for example, tendon cells, and can be and was obtained free of such cells. The isolated native protein has been substantially purified to more than 95% homogeneity.

The isolated native protein, its purified sequenced peptide portion or recombinantly prepared CDS peptide portion, and the CDS protein-specific antibodies which recognize it, are important for the development of therapeutic and diagnostic agents useful for treatment and diagnosis of connective tissues problems, for treatment of injuries and for diagnosis of corrective tissue defects.

The protein is functionally homologous between species, that is, it exhibits similar functional characteristics particularly observable between humans and chicken. The chicken and human tendons are structurally similar and human and chicken collagen is structurally and functionally similar.

Naturally occurring (native) purified avian CDS protein has two active fractions, a 16 kD and 20 kD expressed by primary avian (chicken) tendon cells in culture. The peptide rapidly binds to the cell layer. Such rapid binding restricts the diffusion of CDS and proximally limits the proliferative effect of the peptide.

1. Native CDS Protein

Normal cells in culture are known to respond to cell density by altering their proliferation rates and their pattern of protein expression.

In the parent application, the signaling mechanism for both proliferation and procollagen expression was shown to have the characteristics of a loosely-bound proteinaceous molecule exhibiting a SDS gel migration size of about 25 kD, 35 kD and up to 100 kD.

Figure 6A:
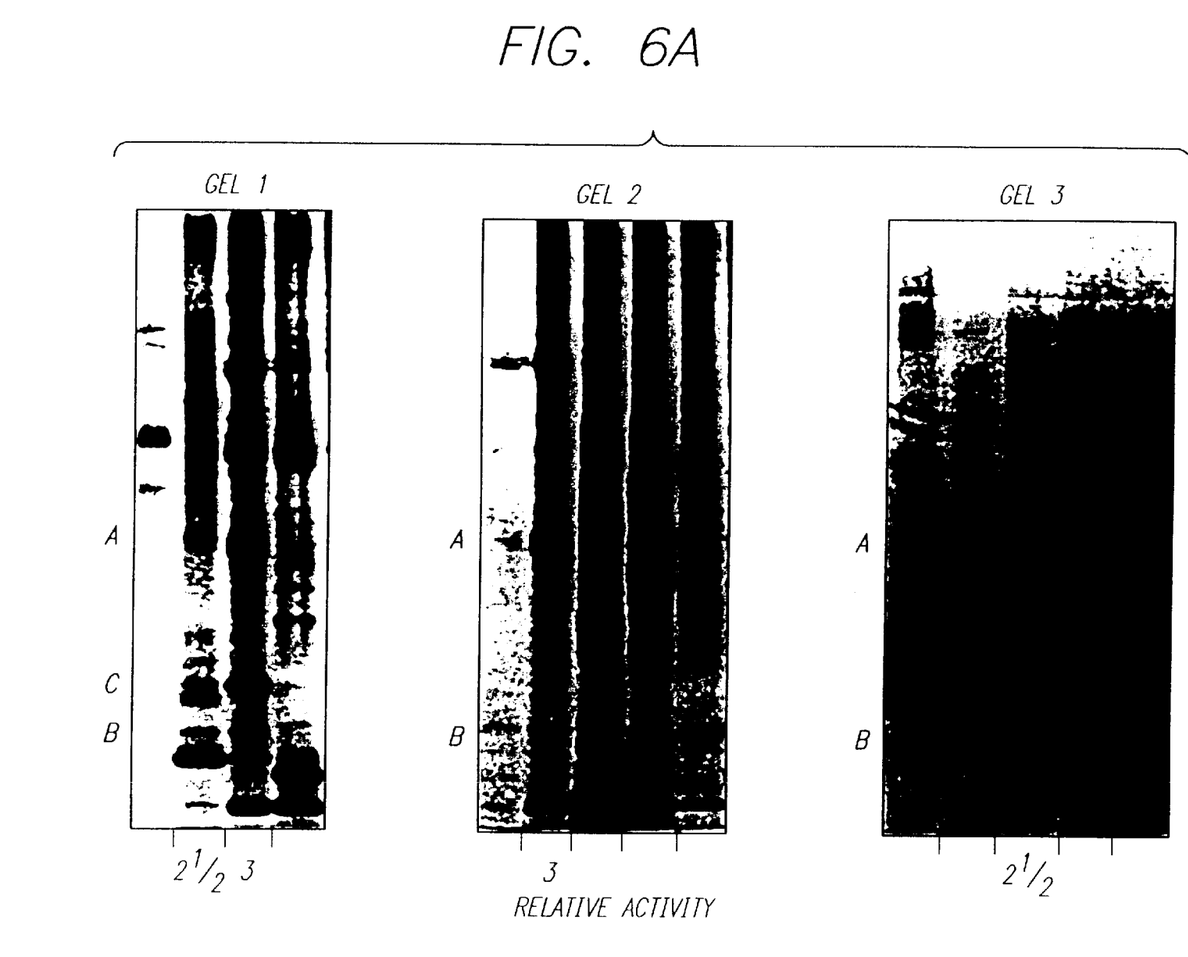
Figure 6B:
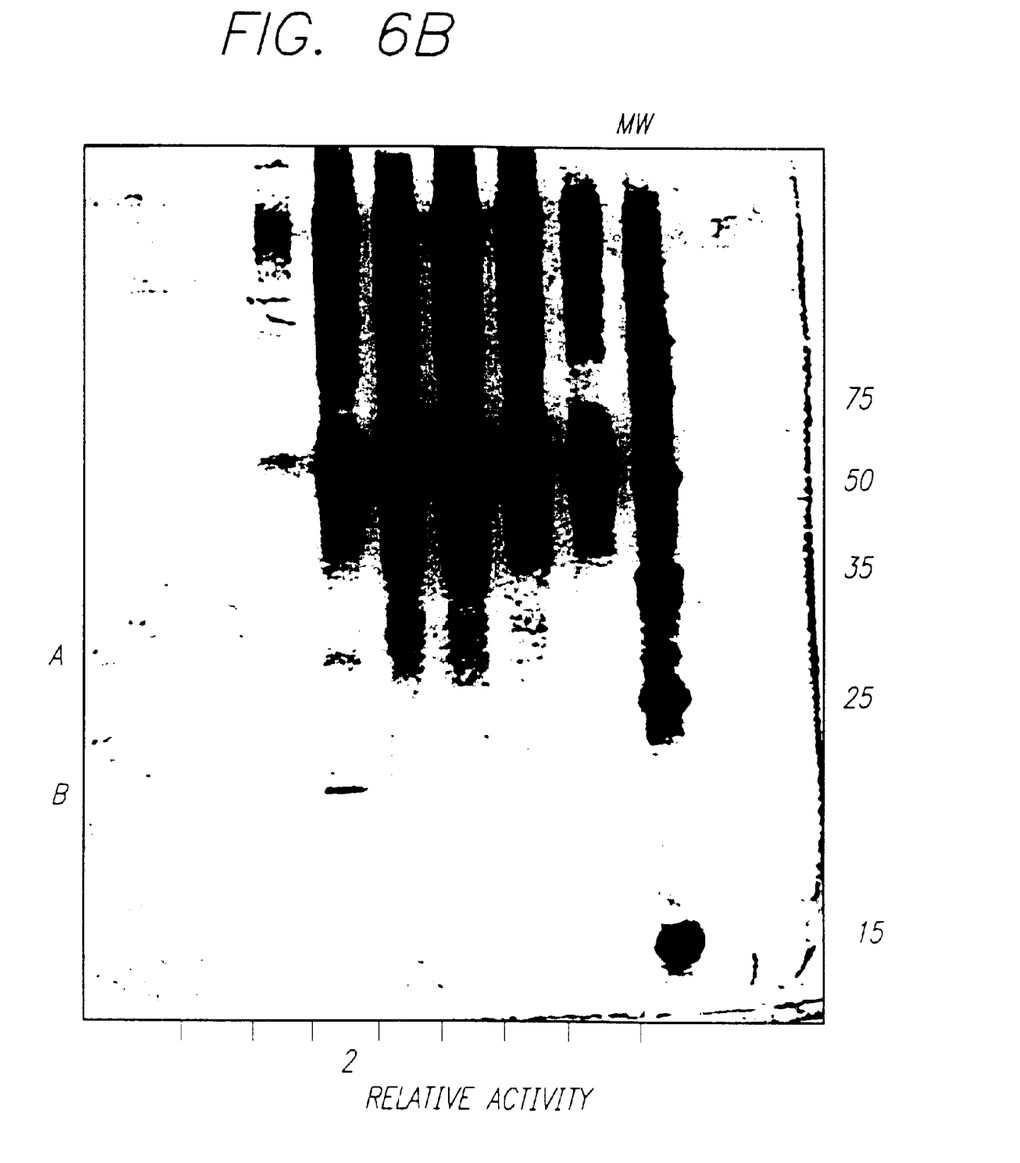

The two newly isolated and purified CDS proteins which are the subject of this invention have biological activity of the cell density signal molecule. A SDS gel migration size of these two proteins are 16 and 20 kD (FIGS. 6A and 6B).

For studies leading to the current discovery, the native avian CDS protein was harvested from cultures of chicken tendon cells by gentle agitation enabling removal of a substantial amount of the CDS protein from the cell layer. The chicken tendon cells, where the CDS protein concentration was reduced, exhibited reduced expression of procollagen, thereby confirming that CDS protein is indeed the molecule responsible for procollagen expression. When added back to cultures of quiescent tendon cells, harvested CDS protein exhibited growth stimulatory activity.

The harvested CDS protein described above was originally found in the medium as a multi-molecular complex with an apparent molecular size of 25–100 kD. After the treatment with a sulfhydryl bond disrupting agent, such as DTT, approximately 30 kD CDS molecule was identified. Upon further purification of this molecule, the two CDS proteins were isolated and found to have a molecular weight of 16 and 20 kD (FIGS. 6A and 6B).

A. Isolation of Native CDS Protein

The native cell density signal protein is produced by fibroblastic cells and can be isolated from the media of cultures of such cells by the process comprising steps of:
  a) preparing fibroblastic cultures of cells derived from avian or mammalian, including human, embryonic cells;
  b) maintaining the cell cultures in a tissue culture cell growth medium, such as F-12 medium obtained from Gibco Co., under appropriate conditions for growth, such as for example, at 37–42° C., at high humidity of about 95%, medium supplementation with serum, and elevated $CO_2$ levels, for from 1 to 5 days, in order to provide moderate to high cell density in the primary culture.
  c) removing the cell growth medium from the cultured cells and replacing it with fresh F-12 medium without serum;
  d) agitating the cultured cells attached to the bottom of flask in the medium of step (c) for multiple one hour collections over several days in order to facilitate release of cell density signal protein (CDS) from the cell layers into the medium;
  e) concentrating the CDS protein from other proteins in the medium, for example, by precipitation, centrifugation, gel filtration, membrane ultrafiltration, and the like;
  f) fractionating the CDS and other proteins to remove low molecular weight contaminants and retain the CDS protein in a high molecular weight complexed form which is retained by a 30 kD exclusion filter;
  g) treating the retained complex with the DTT reducing agent to liberate the CDS protein as a 25–35 kD material; and
  h) isolating the CDS protein as the 25–35 kD material by passing it for example, through a nominal 30 kD filter or the like, and
  i) subjecting the CDS protein of step (i) to purification procedure illustrated in FIG. 6 to obtain purified 16 kD and 20 kD CDS proteins.

The above obtained CDS protein material in step (i), isolated and purified according the Example 2, is a mixture of several small proteins, defined by their sizes of about 16–35 kD, as measured by a SDS-PAGE comparison with known proteinaceous standards.

The mixture of proteins obtained as above in step (i) was then submitted to further purification of step (j), described in detail below in Section 2A and in Example 8, to give two smaller proteins identified as proteins CDS-1 (16 kD) and CDS-2 (20 kD). A portion of CDS-1 fraction was sequenced. Both isolated proteins were tested for their biological activity and have shown enriched growth stimulating activity.

The CDS protein was found to be heat, pH, and DTT stable having retention greater than 75% of the original activity. Additionally, CDS peptide was found to be sensitive to inactivation to less than 40% of original activity by Tris ion, resistant to inactivation by trypsin and sensitive to pronase and proteinase K.

B. Growth and Characteristics of Primary Avian Tendon Cells in Culture

To test the biological activity of the CDS protein and its accumulation in the tissue and to identify the isolate and sequence it, the primary avian tendon cell culture was used. PAT cells were grown according to a protocol described in Example 1.

Primary avian tendon (PAT) cells derived from chick embryos according to Example 1 adapted quickly to the cell culture environment, and as primary cultures, displayed the normal phenotype expected for fibroblasts in culture. At high cell density, PAT cells increased procollagen production about 10-fold, while maintaining proliferation rates near zero.

PAT cells were found to show three cell density effects on cell proliferation. First, they had shown a minimum requirement for cell density in order to grow. Second, they grew rapidly at moderate cell density. Third, there was an inhibition of PAT cell growth at higher cell densities. All of these cell density responses were observed at the same time by establishing a cell density gradient within a PAT cell culture. In this approach, the high medium to cell ratio assured minimizing conditioning effects and at the same time allowed generation of a cell density gradient within the dish.

Under these conditions, PAT cells showed a limited ability to grow out into an area devoid of cells. In contrast, the cells within the initially seeded area grew rapidly until confluent, at which point the cells at the low cell density edge began to die.

Figure 1:
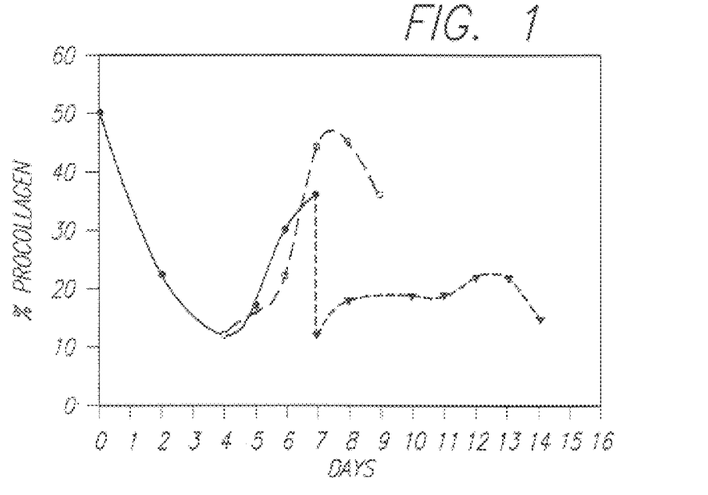
FIG. 1 is a graph illustrating dependence of cell density on the level of procollagen production.
Figure 2A:
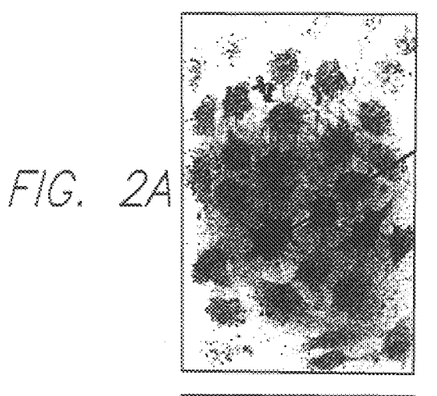
Figure 2B:
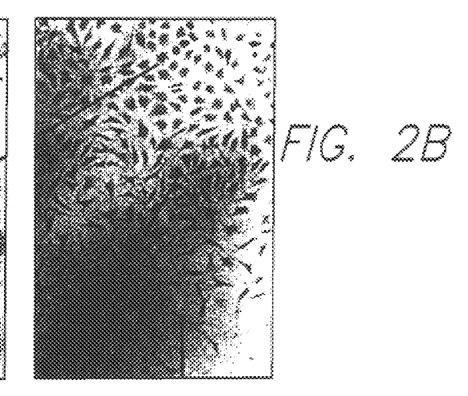
Figure 2C:
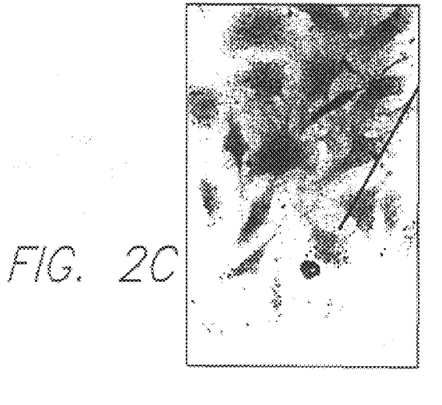
Figure 2D:
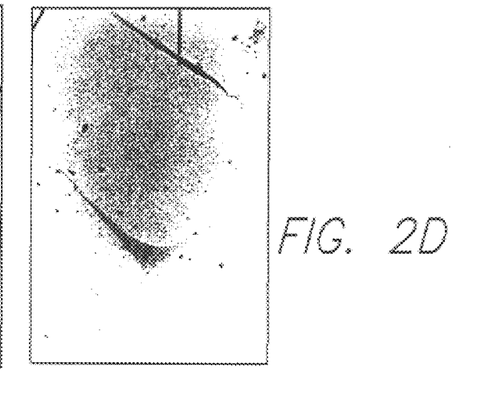

These findings demonstrated that the growth of PAT cells in a cell culture depends on the density of cells. Cell density effects on PAT cells in a permissive cell culture environment is shown in FIG. 1. In this study, the cells were subcultured either on day 4 when the cells were growing exponentially or on day 7 when the cells were approaching a confluent monolayers. The growth conditions were $<2 \times 10^4$ cells/cm$^2$; day 0 was the day when the cells were isolated from the embryo.

In FIG. 1, the solid line is a typical collagen curve obtained by growing the cells from low cell density to a confluent monolayers (day 7).

The dashed line shows subcultured exponentially growing cells which retained their capacity to produce a high level of procollagen on reaching a high cell density up to day 7. However, when the cells have reached the high cell density and the cultures reached a confluent density (dotted line), they were altered and lost their capability to produce a high level of procollagen.

The above results show that the cell density is required for high collagen production but once a high cell density is reached, such high cell density effect on procollagen production is reduced.

While the cell density has been known to influence the procollagen formation of cells, the signaling mechanism controlling this response was until now unknown. To resolve the cell density signaling questions, three assays were used.

A single cell assay was used for quantitative detection of procollagen production using quantitative in situ hybridization. A cell proliferation assay was used to measure thymidine incorporation into cell nuclei. Cell culture conditions, such as shaking of medium, was used to test the release of the CDS at multiple cell densities at one time.

Briefly, for these tests, cells were seeded as a 6 mm island in the middle of a 60 mm dish. Seeding cells as an island in the middle of the dish had the added consequence of increasing the medium to cell ratio by ⁻100 fold. This turned out to be a critical parameter in studies for cell density signalling. Results of these assays are described in Sections C–G and FIGS. 2–5.

C. Assessment of Procollagen Gene Expression

As described above, at high cell density PAT cells increased procollagen production by as much as 10-fold.

Procollagen gene expression was assessed by in situ and dot-blot hybridization method described in detail in Example 3.

In situ hybridization and dot-blot hybridization was used for distinguishing certain cells in a mixed cells population based on the presence of a specific mRNA. This technique allows the most direct and least ambiguous measurement of procollagen expression in correlation between cell density and differentiated gene expression for PAT cells. The technique described in *Mol. Cell. Biol.*, 3:241–249 (1983) was used quantitatively to demonstrate the effect of cell density changes on the amount of procollagen mRNA present in individual cells.

Hybridization conditions were those described in Example 3.

D. Effect of Cell Density on Procollagen Gene Expression

The effect of cell density on procollagen gene expression was based on the results of in situ hybridization described in Example 3.

Previously, the insensitivity of the employed assays required that an average value from over $10^5$ cells be used to analyze cell density changes in the collagen pathway. In situ hybridization assay for procollagen mRNA levels was used for analysis of cell density effects on a cell by cell basis. The effect of different cell densities within the same culture was observed.

Briefly, for these studies, PAT cells were initially seeded inside a 6 mm diameter cloning ring placed in the middle of a standard 60 mm tissue culture dish as described above. After 1 h, when the cells had attached to the dish, the cloning ring was removed. The cells were cultured for 5 days by which time they had become confluent in the middle of the original ring PAT cells showed only limited ability to grow out into the space at the edge of the ring devoid of cells, so that by the end of the 5 days, the circle of cells had only expanded to 7 mm. This expansion was sufficient to establish a low cell density edge while cells in the middle of the circle were at high cell density.

The cell density distribution caused a wide variation in procollagen mRNA levels. The cells at a confluent density in the center of the ring contained high levels of procollagen mRNA as evidenced by the large numbers of exposed silver grains over them. In contrast cells at the low density edge had low levels of procollagen mRNA.

In those experiments where the cells were initially restricted by cloning rings there was a very high ratio of medium volume to cell number yet the cells remained responsive to cell density.

In situ hybridization for procollagen mRNA is shown in FIG. 2. In situ hybridization utilizes a probe for procollagen mRNA in cells grown as an island in the middle of the disk, as seen in FIG. 2. A section of the island of cells is shown in the upper right panel FIG. 2B where the distance from top to bottom is 1 mm. Lines are drawn to the same cell in the enlargements. The cells at the low density edge (lower right panel; FIG. 2D) had an average of 4±3 exposed grains ($^3$H) in the photographic emulsion over each cell; at moderate density (lower left panel; FIG. 2C) 18±9; and at high cell density (upper left panel; FIG. 2A) 31±9. These findings demonstrate the cell density effect on collagen production. There is a gradient of cell density over about a 1 mm distance. Cells that are more than 1 mm from an edge behave as other cells and do not reflect decreasing cell density gradient as they are approaching an edge. This distance is about 20 cell diameters and is more readily explained by the presence of a diffusible factor than with communication by cell contact. On the other hand, the island of cells was grown in large amounts of medium and yet this has no effect on the ability of cells to detect their neighbors as seen in FIG. 2. Cells in the middle of the island grow to the same cell densities and make the same high levels of collagen as cells that are evenly distributed over the dish.

Results show that confluent cells express differentiated function but retain capacity for cell division.

In situ hybridization confirmed the dependency of procollagen expression on the cell density. The cells that were at moderate cell density in the middle of the island of the cells produced high levels of procollagen as the cell density increased. In contrast, low cell density resulted in low levels of procollagen expression.

E. Cell Density Signal Molecule

From the results described above, it is clear that the cell density controls a procollagen gene expression. Procollagen expression is proportional to cell density.

To further test the signal molecule is tightly or loosely bound, the cells were gently agitated in the incubator and collagen production was measured by in situ hybridization with a procollagen probe. This study indicates that the signal molecule is bound loosely and can be released into the medium when the medium is subjected to shaking, but if there is a high cell density to sufficiently condition the medium, shaking has no effect.

F. Cell Proliferation—Thymidine Incorporation

To measure increase in cell proliferation in response to the CDS protein stimulation, an assay detecting thymidine incorporation into cell nuclei was used. $^3$H thymidine uptake by the cells was measured following the cell stimulation with CDS-1.

The effectiveness of conditioned medium at stimulating cell proliferation was dependent on the surrounding cell density. With cells seeded as an island in the middle of the dish, cells at the low cell density edge were stimulated at a lower concentration than those at high cell density in the center. In addition, even when sufficient conditioned medium was added to stimulate cells in the center of the island, this concentration was insufficient to stimulate cells at the same high cell density but confluent over the whole dish. This was an indication of a relationship between the absolute amount of factor added and the number of cells in determining whether the cells would proliferate. This was tested by concentrating the conditioned medium sixfold by ultrafiltration through 30 kDa exclusion membrane and using cells seeded evenly in a 12-well plate and grown until confluent, at which time, various amounts of the concentrate were added (Table 1) and the change in proliferation rates are quantitated by ($^3$H)thymidine uptake over a 24-h period. In this case, 0.25 ml of the concentrate would equal the original ratio of conditioned medium to cell number in the flasks used to make the conditioned medium and at this concentration there is an ⁻20% increase in thymidine incorporation. Results are seen in Table 1.

TABLE 1

| Increase in $^3$H Thymidine Uptake on Addition of Concentrated (6x) Conditioned Medium | |
|---|---|
| Milliliters | Counts Per Minute |
| 0 | 21 108 |
| 0.1 | 21 025 |
| 0.25 | 26 870 |
| 0.5 | 44 078 |
| 1 | 68 706 |
| 2 | 75 281 |
| 3 | 92 087 |
| 4 | 79 565 |
| 5 | 99 364 |

*Each point is single determination except 0 ml which is the average of 4.

Results seen in Table 1 show that CDS-1 stimulates proliferation of cells.

G. Properties of Shaken Conditioned Medium

The cell growth activating properties of the CDS molecule depends on its presence or absence in the culture medium. This points toward loosely bound molecule which is easily released into the medium.

Figure 3A:
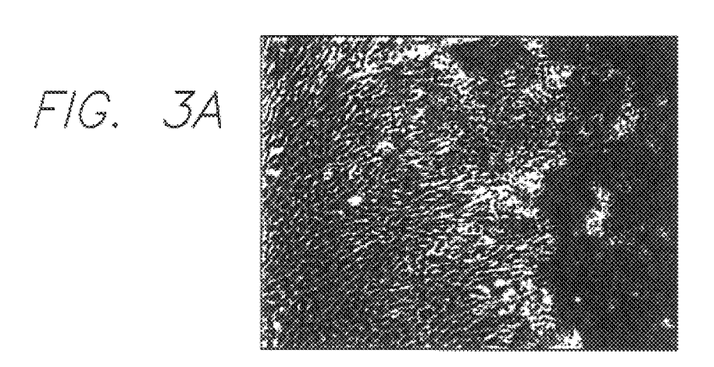
FIG. 3A are control cells.
Figure 3B:
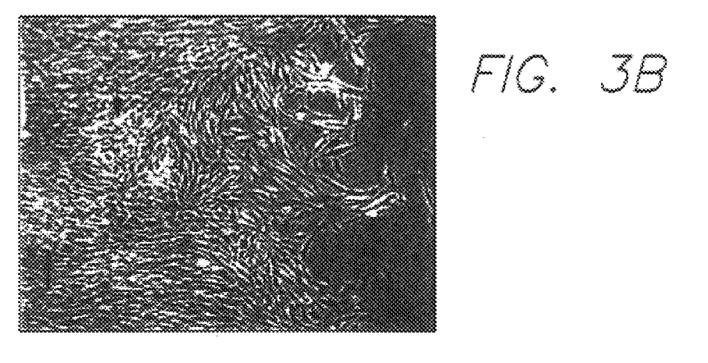
FIG. 3B are cells grown on shaken conditioned medium.

To investigate this, properties of shaken conditioned medium were determined in the shaken conditioned medium placed in PAT cells grown as an island. Two days later the cells were photographed under phase contrast microscopy. Results are shown in FIG. 3. Control cells (FIG. 3A) were grown in regular F12 medium and 0.2% serum. Conditioned shaken medium caused the cells to grow (FIG. 3B).

H. Physical Characteristics of CDS Peptide

CDS activity as a growth stimulator was used to assay its presence and allowed its characterization and purification.

a. Ammonium Sulfate Precipitate

CDS was found to be stable to ammonium sulfate precipitation and could be concentrated >100-fold. At this concentration a small amount was tested under various conditions and then diluted into medium to test the retention of activity at a 1× concentration.

b. CDS Stability and Low pH Sensitivity

CDS retained at least 75% of its biological activity after exposure to low pH (50 mM sodium acetate, pH 5.2 for 60 minutes), disulfide bond reduction (10 mM DTT, for 30 minutes) and heat (90° C. for 10 minutes). It was also stable in medium or PBS for months at 4° C.

c. Tris Ion Sensitivity

Exposure to Tris ion (50 mM Tris pH 7.5 for 60 minutes) resulted in the loss of greater than 90% of CDS biological activity, while Tris base (50 mM Tris pH 8.8 for 60 minutes) had little effect (retention of greater than 90% biological activity). Exposure to 10 mM EDTA inhibited biological activity.

d. Proteolytic Sensitivity of CDS

The CDS was tested for sensitivity to proteolytic digestion with proteinase K (P9290-Sigma), pronase (P4531-Sigma) and trypsin (T-8386-Sigma). Binding the enzyme to agarose or acrylamide was used to facilitate removal of the enzyme after the reaction. The bound enzyme (1 unit) was washed 2× in basal medium (30 mM), on a rocking platform. Then the medium containing 1×CDS was treated for 2 hours at 39° C. with rocking, spun in a table top centrifuge and filter sterilized. Basal medium was treated similarly and used as a control. Serum and ascorbate was then added to each sample and the CDS was tested for biological activity.

The CDS peptide was insensitive to trypsin (greater than 75% of biological activity retained) but was sensitive to both protease enzymes, proteinase and pronase, retaining less than 10% of biological activity. Protease digestion of CDS also resulted in a toxic response to all the cells tested. A similar toxicity developed in CDS samples that were repeatedly freeze thawed.

I. Purification of CDS Mixture

Since the CDS mixture was stable when subjected to several treatments that disrupt aggregation, the heat, pH, and DTT treatments were used to determine whether they altered the chromatographic properties of CDS on a Bio-Gel P-30 column.

Figure 4:
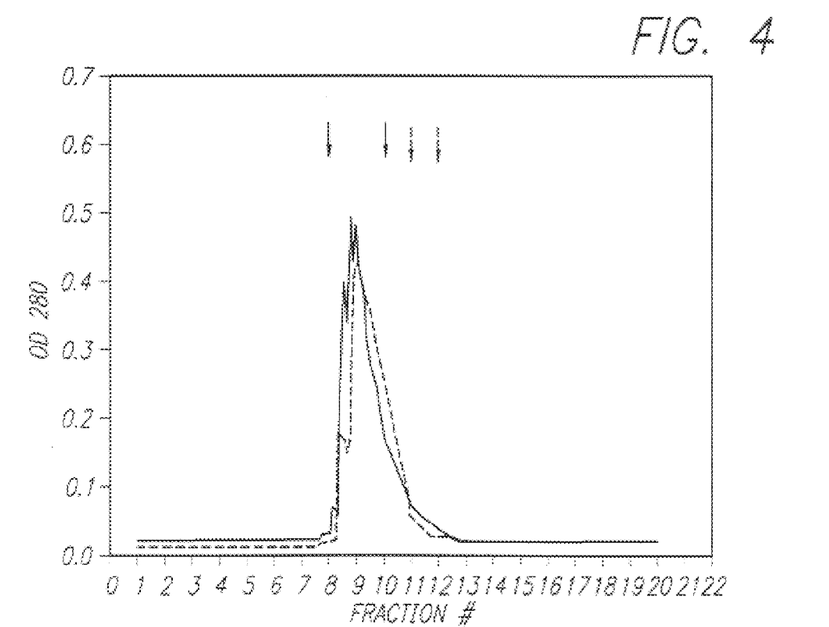
FIG. 4 is a graph showing the chromatographic separation of proteins isolated from primary avian tendon cells. The continuous arrows mark the range of CDS activity prior to DTT treatment and the dashed arrows mark the range of activity after DTT reduction.

Of those above, only DTT addition had any significant effect. After DTT treatment, most of the CDS activity was eluted, not in the flow through, but in the fractions just following the void volume peak, showing some penetration of CDS into the pores of the gel. Results are seen in FIG. 4, where continuous arrows denote fractions containing CDS activity prior to DTT treatment and the dashed arrows denote fractions containing CDS activity after DTT treatment. This demonstrated that the active component of native CDS is a molecule in the range of 25–35 kD which is found in an aggregated, possibly multimeric, form in the medium of agitated cell cultures. After treatment with DTT, the manometric 25–35 kD molecule retained CDS activity. This information was used to develop a purification protocol for subfraction of CDS mixture.

For purification of native CDS, the medium from agitated cultures was concentrated by ammonium sulfate precipitation and the concentrate was ultrafiltered using a 30 kD exclusion membrane. All the activity was retained in the >30 kD fraction. Then, the retenate was treated with 10 mM DTT for 30 minutes and again ultra filtered using a 30 kD membrane. About half of the activity now passed through the filter. The activity from the flowthrough (the equivalent of 50 ml of conditioned medium) showed no bands on SDS-PAGE after silver staining. Yet, this material retained its biological activity.

When the conditioned medium was used from cells labeled overnight with high levels of radiolabeled amino acids, subjected to the same fractionation procedure above, run on SDS-PAGE, and fluorographed, a single diffuse band was observed, with an apparent molecular weight of approximately 30 kD (FIG. 4). In FIG. 4, the left lane was loaded with the retenate of a DTT treated 30 kD ultrafiltration procedure and the right lane was loaded with the flowthrough.

J. cDNA Library and Sequencing

Primary avian tendon cell cultures were used to prepare a cDNA library which was then screened for particular DNA sequences that encode CDS specific polypeptides.

Preparation of cDNA library and sequencing of CDS is described in Examples 5 and 4, respectively.

K. Analysis of Mammalian Genomic sequences of CDS DNA

CDS-encoding genes are obtained from genomic libraries of chickens available from Clontech, Palo Alto, Calif. or of various mammals, generally available, in phage, from the ATCC or commercial sources. For example, a human genomic library of fetal liver cells in Charon 4A phage is available (ATCC 37333).

Briefly, the library contains $10^6$ independent recombinants with an insert size of 15–20 kD and it is screened with cDNA by using methods known in the art.

The stringency of the hybridization solution is adjusted to account for the non-homology between the avian and mammalian CDS polypeptide. Stringency is lowered to increase the tolerance for mismatch in the hybridization by raising the salt concentration and/or lowering the temperature of the hybridization. The degree of non-homology varies within different regions of functionally homologous polypeptides. Generally, the sites of functionally homologous activity demonstrate the greatest degree of homology. These sites are predictable based on analyses of the structure of the avian CDS polypeptide.

The cell density signal molecule mixture acting as a growth simulator was isolated, identified and tested for its properties, as described in sections 1A–B. In the context of the Section 1, the CDS molecule is contained in a mixture of proteins having a molecular weight between 25 and 100 kD.

2. Isolated, Purified and Partially Sequenced CDS-1 and CDS-2 Proteins

Recently, the native CDS protein mixture described in Section 1, obtained as described below, has been purified to two bands on SDS-PAGE, two bands were identified and isolated and the biological activity of these bands was correlated with CDS stimulatory activity. This purified CDS is identified as CDS-1 and CDS-2 proteins of 16 kD and 20 kD. The CDS-1 protein was partially sequenced at its N-terminus.

A. Purification of the CDS-1 Sequence

CDS-1 and CDS-2 (Cell Density Signal—1 and 2) proteins had been purified to two bands on SDS PACE. The detailed purification procedure is described in Example 8 and illustrated in FIG. 5.

The purification up to 95% homogenity enriched biological activity of CDS proteins from between 10,000 to 100,000 fold. Maximal growth activity in the assay was obtained at about 500 pg/ml of the purified protein, which confirms that the CDS protein is biologically extremely active molecule.

The band's intensity increased with the degree of purification which correlated with increased biological activity. Purification method consisted of shaking primary cultures of avian tendon cells in a serum free medium for one hour and repeating this up to five times a day from day 4 to day 7, concentrating the medium by ultrafiltration through a 10 kD ultrafilter and testing them for biological activity.

Following this process, the active fraction was found to be present almost completely in the filter retentate. The retentate was then applied in sequence to four columns. The purification procedure is illustrated in FIG. 5.

In order to obtain a sufficient quantity of sufficiently pure molecule for sequencing, purification procedure of the CDS protein mixture demanded development of specific purification process. This was complicated by the fact that molecules that are loosely bound to the cell layer do not have to be present in large quantities to work effectively. For the purification protocol this means that the activator is there in minute quantities. This makes the purification difficult, however this is compensated for by the fact that the activator molecule is extremely stable. The purification scheme, therefore, had to be optimized so that the greatest purification could be obtained in the fewest columns. A good column gives a 10 fold purification but with a 50% loss in material. FIG. 5 shows the step sequence of the specifically developed purification process for CDS protein.

Figure 5:
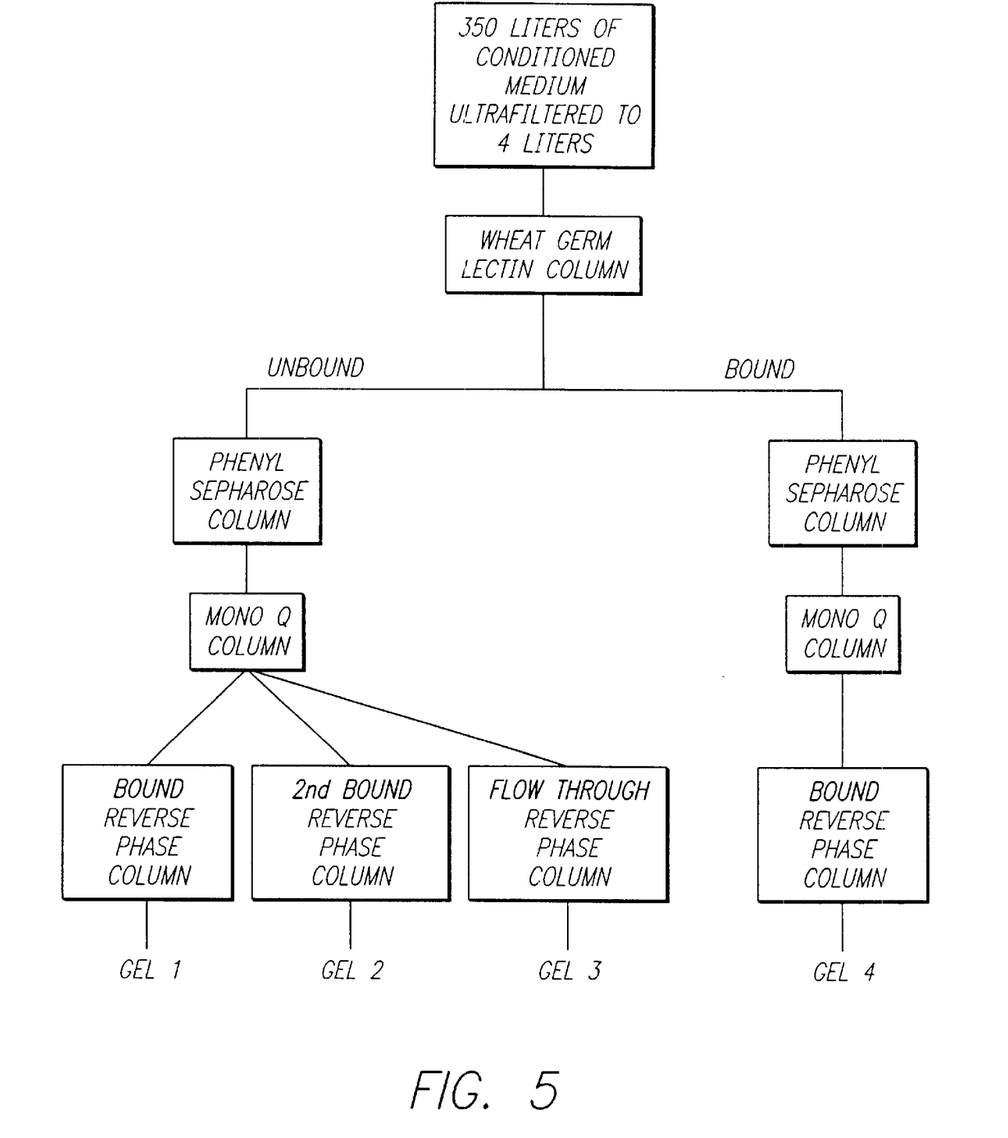
FIG. 5 is a scheme of purification procedure for purification of a cell density signal molecule.

FIG. 5 is a flow diagram summarizing the purification procedure. Starting with about 350 liters of shaken conditioned medium that is ultrafiltered, samples are run through 4 columns, and the final fractions from these separations are analyzed by SDS polyacrylamide gel electrophoresis. A critical branch point in the purification procedure is after the first column where part of the active material binds to the lectin column and is assumed to be more glycosylated resulting in CDS-2 (kD 20) and part of the active material flows through resulting in CDS-1 (kD 16). The unbound material from the first column also had difficulty binding to the third column, mono Q, resulting in three subgroups. In this instance, a four column procedure, as seen in FIG. 5, was used. Purification started with large amount, (350 liters) of shaken conditioned medium to end up with around a μg of material available for protein sequencing. The starting conditioned medium contained 15 g of CDS protein mixture which needed to be purified 200,000 fold, including the SDS gel as the last step. In the beginning, 1 mg/ml of the CDS protein mixture was needed to give the full biological activity in the assay for CDS. By the end of the purification process, 500 pg (picograms) of the purified CDS protein have shown to give the equivalent full biological activity, with detection threshold of 10 fold less, that is about 50 pg. Compared to other growth factors which were shown to affect tendon cells, these other factors are at least 10 to 100 fold less active.

As seen in FIG. 5, the first column was wheat germ lectin column. In the first separation, some of the activity was found to have remained bound (bd fraction) to the wheat lectin column while some of the activity flowed through as unbound (ft fraction). Both fractions were then separately applied to the second phenyl sepharose column in high salt concentration. Both bd and ft fractions were bound to this second column. When the salt concentration was lowered, active material eluted. This material was diafiltered and applied to the third mono Q column. Afterwards, it was again eluted and applied to the fourth, reverse phase, column.

After column separation, an aliquot of active bd or ft fractions was run on SDS-PAGE. For bd fraction, a clear band at 20 kD was observed. For ft fraction, a clear band at 16 kD appeared.

Two bands obtained by SDS-PAGE gels correspond to two individual proteins, 16 kD CDS-1 and 20 kD CDS-2.

SDS-PAGE gels of both the unbound (ft) and bound fractions (bf) are shown in FIG. 6A and FIG. 6B. The gels 1–4 seen in FIGS. 6A and 6B correspond to purification fractions, as seen in FIG. 5. These bound and unbound fractions are obtained after the first separation step on wheat germ lactin column.

FIG. 6A shows separation of proteins on SDS-PAGE gels 1, 2 and 3, also corresponding to those fractions obtained during the last step of purification separation of the unbound fraction from wheat germ lectin column (FIG. 5). The fractions 1, 2 and 3 obtained from the reverse phase column correspond to gels 1, 2 and 3 in FIG. 6A. In FIG. 6A, the bottom legend shows the relative biological activity over background. In a reducing gel, the biological activity is expected to run below 30 kD. As seen in FIG. 6A, there are three bands, A, B and C, which are below 30 kD and whose concentration correlates with biological activity. The apparent molecular weights of these bands are 28 kD (A), 16 kD (B) and 20 kD (C). Sequencing of these bands showed that the A band was a procollagen propeptide, a known contaminant. Sequencing of the band C showed that it is a tissue inhibitor of metaloproteinases (TIMP), also a known contaminant. Sequencing of the third unbound band showed that the band B is unique to known sequencing in the public domain databases. The band B, having 16 kD molecular weight corresponds in the biological activity to CDS-1 protein showing a cell growth stimulating activity at 500 pmoles/ml amount. This protein comprises at its N-terminal end of the 14 amino acid sequence identified as SEQ ID NO:1, or any of its fragments, variants, mutants or analogs as long as they do not change its growth stimulating activity.

The bound fraction, further sequentially separated on phenyl sepharose, mono Q and reverse phase column is shown in FIG. 6B as gel 4. The gel 4 shows separation of proteins on SDS-PAGE of the fractions obtained from the reverse phase column. The bottom legend shows the relative biological activity over background. The MW lane shows molecular weight markers in kD. Approximately 2% of the total material from the reverse phase column fraction was loaded into the gel. As seen in FIG. 6B, two primary bands were obtained. The A band had an apparent molecular weight of 28 kD. The B band had an apparent molecular weight of 20 kD. There was insufficient quantity of these materials for sequencing.

B. CDS-1 Fraction Sequencing

The intensity of the 16 kD band correlated with biological activity and the band's intensity increased with degree of purification. This band was reproducibly found in the purified active fractions.

Following the purification, the estimate based on the amount of protein added to the assay is that the most purified fractions are between 10,000 and 100,000 fold enriched for the cell growth stimulating activity. The activity based on an estimation of protein concentration from the intensity of bands on a silver stained gel is that 500 pg/ml gives full activity. Detectable levels are 10 fold less. The isolated purified CDS-1 protein was found to be an extremely active factor.

The active fractions from last steps the purification scheme were run out on SDS PAGE, blotted onto a membrane, and put into an automated N-terminus protein sequencer. The primary candidate band, 16 kD, was sequenced several times, each time giving the 3 amino acid sequence, Glu-Pro-Leu. In order that enough protein was used to obtain a longer sequence, several fractions were combined. This gave the N-terminal sequence of 14 amino acids, EPLAVVDLTEKTIS, (SEQ ID NO:1) with the most confidence in the amino acids closest to the amino end. Other bands which were also sequenced turned out to be known contaminants.

The 20 kD band which was not yet sequenced is likely to be similar to the 16 kD band but with significant increase in glycosylation.

C. Screening a cDNA Library Made from Chick Tendon mRNA Cells or a Genomic Chick Library A genomic library is commercially available. For a cDNA library, many molecular biology kits are available to produce them. Basically, mRNA is reversed transcribed into DNA, and the DNA inserted into plasmids or viral vectors. These libraries of mRNA sequences or genomic sequences are screened with labeled oligonucleotide (usually 12 nucleotides or larger) corresponding to the protein sequences of at least 4 amino acids to fish out the right clone. Because the genetic code is redundant, there are many nucleotide sequences for any given amino acid sequence. The clones that hybridize to the short nucleotide sequence can be sequenced to determine that they code for the known 14 amino acid sequence. The 14 amino acid sequence is then extended to full length protein.

The obtained clones can be used for investigation whether other tissues, especially other connective tissues (bone, cartilage, the dermis of skin, etc.,) also express CDS-1. Using RNA from these tissues, a Northern gel is run, the gel is blotted and hybridized to a probe containing the sequence complimentary to CDS-1 mRNA. It is expected that other connective tissue such as bone, cartilage, skin, etc., use a similar cell density signaling mechanism.

The clones at low hybridization stringency are used to select clones from mouse or human genomic libraries. In this way, the human and mouse equivalents are determined. Since the morphology of the tendon and the major differentiated product of tendon, collagen, are similar between avian and mammalian species, as discussed above, the human CDS is also highly conserved.

D. Antibodies to CDS-1 or to 14 Amino Acids Peptide

Antibodies to the CDS-1 protein or its N-terminal 14 amino acid fragment are prepared by methods known in the art.

The 14 amino acid sequence (SEQ ID NO:1) or a protein comprising the SEQ ID NO:1 is synthesized in sufficiently large quantities to immunize rabbits for production of polyclonal antibodies or to immunize mice and screen a hybridoma library for monoclonal antibodies.

The obtained antibodies speed the purification procedure, and are useful in understanding the interaction of CDS-1 with other molecules. Human forms are useful therapeutically in controlling overgrowth of some connective tissues, such as for instance, in Keloid formation in the skin or for detection purposes.

II. Biological Properties of CDS Peptide

The CDS protein is characterized by its biological properties, such as the ability to initially stimulate the proliferation of embryonic tendon cells in culture and thereafter promote the expression of a differentiation function, namely procollagen gene expression.

A. Biological Activity of the CDS Released Into the Medium
 1. Stimulatory Effect CDS-1 protein was determined to act as a promoter of procollagen gene expression and to be growth stimulatory.

To confirm these findings, confluent cultures of PAT cells were agitated in the minimum amount of medium that would cover the dish (1 ml), thereby releasing CDS into the medium. This medium was applied to cells initially seeded in cloning rings. Then 5 ml of this conditioned medium was used on the test cells. This gave about a 500 fold increase in the amount of CDS available to each cell. The test cells were grown for 5 days before conditioned medium was added, and then two days with it. PAT cells receiving the conditioned medium were dramatically stimulated to divide. At higher concentrations, even the cells that were at a confluent density could be induced to divide. In contrast the control plates showed large amounts of cell death at the edge of the circle of cells.

Thus, in the case of a uniformly confluent culture, shaking releases a factor which is stimulatory for the proliferation of a homologous culture. The CDS-1 CDS-2 proteins isolated, purified and partially sequences assert the same effect when added to the cell culture.

III. Therapeutic Properties and Utility of CDS Peptide

CDS proteins have therapeutic and diagnostic utilities. The proteins may be used for treatment of tendon or ligament injuries, for example, by administering to the site of injury a sufficient amount of CDS protein comprising 14 amino acid peptide of SEQ ID NO:1, or any fragment, variant, mutant or analog thereof which has the same biological activity. The CDS protein is administered in an amount which will stimulate expression of procollagen leading to higher production of collagen or which will stimulate growth. Stimulation of cell growth will promote faster healing and repair of the tendon or ligament injuries or other connective tissue.

For diagnostic purposes, for example to detect connective tissue defects, the CDS protein-specific antibody is used to detect low levels, absence or deficient dysfunctional CDS protein.

The CDS protein is administered in oral or parenteral form, as injectable, tablet, suppository and other pharmaceutically acceptable formulations. The CDS protein formulation may contain other pharmacologically active compounds to enhance its therapeutic effect and/or pharmaceutically acceptable additive and excipients.

EXAMPLE 1

Growth of Primary Avian Tendon Cells in Culture

This example describes a primary avian tendon cell culture protocol used for growth of PAT cells.

Primary avian tendon cells were isolated from 16 day chick embryos by a modification of the method described in *Biochem. Biophys. Acta.*, 240:358–369 (1971), incorporated by reference. Unless otherwise specified, cells were seeded onto 25 $cm^2$ tissue culture flasks and grown in F12 medium supplemented with 0.2% fetal bovine serum and 50 (μg/ml absorbate.

When a large medium-to-cell ratio was required, cells ($10^4$) in medium without serum were seeded inside a glass cloning ring (6 mM inside diameter) that was placed within a standard tissue culture plate (60 mM diameter). Medium was placed on the outside of the cloning ring to equalize hydrostatic pressure. After 1 h, when the cells had attached, the cloning ring was removed. The medium was changed to F12 medium (5 ml) supplemented with 0.2% fetal bovine serum (Gibco) and with 50 µg/ml of absorbate.

EXAMPLE 2

Purification of Native CDS Peptide

In order to identify the peptide and to obtain its sequence for cloning, the native CDS was isolated from cell culture and purified. This example described the method and condition used for purification.

Growth medium with 0.2% serum was replaced with basal medium obtained from Gibco (6 ml of F12 medium for 150 cm² flask) on high cell density cultures and the cell medium mixture was shaken gently (60 rpm on a rotary shaker) at about 39° C. for 1 h. This was repeated twice a day for 4 days. The cell-free conditioned medium was stable for several months when stored at 4° C.

Ammonium sulfate was added to make a 40% to 60%, preferably a 50% saturated solution (4° C.) and left overnight. The solution was spun at approximately 35,000 rpm for 30 mM (45Ti rotor, Beckman). The pellet was resuspended in phosphate buffered saline (PBS) and concentrated by ultrafiltration (30 kD exclusion filter, CX-30; Millipore). The concentrate was diluted again and reconcentrated to further reduce the concentration of ammonium ions which are toxic to cells. The final concentration was adjusted to a concentration of 100× when compared to the original medium volume. Dilution to 1× concentration gave approximately equal growth stimulating activity as the original conditioned medium.

The concentrate was treated with 10 mM DTT (dithiothreitol) for 30 minutes at 37° C. and the mixture was again passed through a 30 kD ultrafilter (PF-30, Millipore). The ultrafiltrate retained about half the biological activity as the original medium.

To label CDS, cells (25 cm² flask, 5 ml) were labeled with 1 mCi of radioactive amino acid in growth medium overnight. The labeled medium was removed and basal medium (1 ml) was added and the mixture was conditioned by shaking, as described above. The ammonium precipitation step was not required and the medium was concentrated and diluted with PBS several times to reduce the levels of unincorporated label. Finally, this mixture was concentrated to 100 µl and treated with DTT, as above. After 30 kD ultra filtration both the filtrate and retenate were applied to an SDS PAGE gel (3% stacking, 15% resolving). The gel was impregnated with Enhance (NEN) and exposed to X-ray film at −70° C.

EXAMPLE 3

In situ Hybridization

This example describes in situ hybridization for detection of a CDS specific mRNA.

PAT cells were fixed with 4% paraformaldehyde in PBS (10 mM) followed by washing in 0.1 M glycine in PBS. After fixation, the cells were covered with 2 ml of hybridization solution (60% deionized formamide, 0.1 M PIPES pH 6.4, 0.4 M NaCl, 5% poly A RNA [2.5 mg/ml]). After prehybridization for several hours at 55° C., the hybridization solution was changed, labeled probe was added, and the cells were hybridized for 48 h. Unless otherwise stated, $2 \times 10^6$ cpm of the labeled probe was used with a specific activity of $3.3 \times 10^7$ cpm/µg.

After hybridization, the cells were washed twice for 1 h in 0.1% Triton X-100 in 2×SSC at 55° C. and then twice for 1 h in 0.1% Triton X-100 in 0.1×SSC at 60° C. The cells were dehydrated with graded alcohol washes and then covered with photographic emulsion (NBT2, Kodak). Development times varied depending on the specific activity of the probe. With the standard specific activity as above, the exposure time was 2 weeks. Several early experiments used a 2-fold higher specific activity probe (by labeling with both $^3$H-ATP and $^3$H-UTP) and exposure time was correspondingly shortened to 1 week. The cells were stained with Wrights.

In experiments quantifying the amount of $^3$H-RNA probe hybridized, the cell layer was solubilized using 1% SDS and the level of radioactivity measured by scintillation counting.

Fixed cells were treated in the same manner as in dot-blot hybridization where the volume of hybridizations solution was on the order of mls, no pretreatments other than prehybridization were used and only salt and detergent solutions were used in the post-hybridization washes.

EXAMPLE 4

Sequencing of CDS

This example describes the procedure used for sequencing of CDS-1 protein. Purified CDS isolated from SDS gel is sequenced by subjecting up to 100 pmoles (estimated from staining intensity on acrylamide gels) to automated Edman degradation utilizing an Applied Biosystems 477A pulsed liquid phase protein sequenator.

N-terminal sequencing may not be adequate to clone the cDNAs of the CDS. For instance, the CDS may be blocked or modified at the N-terminal or alternatively, the N-terminal sequences may not show favorable regions for generation of oligonucleotide probes. In such case, the CDS was digested with a protease according to *Antibodies: A Laboratory Manual*, Cold Spring Harbor Press, 1989) and the peptide fragments were purified in order to generate additional sequence information. In these cases the protein was concentrated to a 5 µl volume by vacuum centrifugation, and then digested with the protease. Protease fragments were purified by reverse phase HPLC using a Brownlee RP 18 narrow bore column and an Applied Biosystems 130A liquid chromatography designed specifically for purification of pmole samples.

Sequence data thus obtained were compared to known protein sequences by computerized searches of the Protein Identification Resource of the NBRF, and of the Swiss protein database, in order to determine their novelty or relationship to other protein sequences.

EXAMPLE 5

Screening of cDNA Libraries

This example describes procedures and conditions used for screening of cDNA libraries. Techniques for the preparation of a cDNA library are known and described in laboratory manuals and known to those skilled in the art. The preparation of the cDNA libraries is described in detail in Maniatis, T. et al, *Molecular Cloning*, (1982), CSHL Press. A convenient approach is the insertion of cDNA fragments into a lambda phage vector, e.g. lambda gt10 or lambda gt11 as described by Maniatis, supra.

Methods of screening cDNA libraries are also well known to those skilled in the art. The amino acid sequence of the CDS was analyzed utilizing programs from DNAStar (Madison Wis.) in order to identify optimal regions for construction of oligonucleotide probes. Redundant oligonucleotide probes were synthesized with a DNA synthesizer (380A: Applied Biosystems Inc., Foster City, Calif.) by the phosphoramidite method. oligonucleotide were purified on Sephadex G-50 columns and stored at −20° C. The redundant probes were 5'-labeled with (theta)-[$^{32}$P]ATP (E. I. du Pont de Nemours & Co. Inc., Boston, Mass.) using T4 polynucleotide kinase.

Libraries were screened using up to $10^6$ individual plaques per library, with the redundant oligonucleotide probes. Duplicate nylon membranes containing phage were prepared and prehybridized in Sx SSPE (0.9M NaCl, 50 mM $NH_2PO_4$, 5 mM EDTA, pH7.4), 0.2% SDS, and 0.005% denatured salmon sperm D⁻A for 2 hours at 50° C. with 8 filters per 50 ml prehybridization fluid per bag. Membranes were hybridized with approximately 1 ng of labeled probe per ml, in fresh hybridization fluid, overnight at the appropriate temperature for the redundant probe mixture. Membranes were then washed at room temperature for 45 minutes in 1 liter of Sx SSPE per 40 filters, followed by a 1 minute wash in fresh buffer at 50° C., slightly air-dried, and exposed to Kodak XAR-5 film, with intensifying screens, for 72 hours at −70° C.

After analysis, filters were stripped of hybridized label by incubation in 5x SSPE at 70° C. for 10 minutes and subsequently hybridized with a second probe. Probes were selected from the library and plaque purified.

Recombinant phage DNA was then purified and digested with an appropriate restriction endonuclease to yield the amplified cDNA insert. Inserts were then ligated into M13mp series phage and sequenced using the "dideoxy" method described in *Proc. Nat. Acad. Sci.*, 80:3963 (1983). Depending on the size of the cDNA, the clone may be restricted, and the fragments subcloned the fragments into M13. When the cDNA clones were not complete, a repeat screen of the library with the partial cDNA was performed.

The complete sequence of the CDS cDNA was then compared against known sequences in the GenBank database. DNAStar was used for nucleotide and polypeptide analyses and sequence comparisons.

Selected cDNA inserts which encode CDS were then incorporated into an expression system. The cDNA was operably linked to heterologous control sequences to form an expression vector. The control sequences were chosen to be functionally compatible with the recombinant host cell into which the expression vector was introduced.

Procedures for screening DNA libraries and cloning DNA encoding CDS are known to those skilled in the art and described in *Molecular Cloning* (1982).

Expression of the DNA can be in procaryotic or eucaryotic systems. Prokaryotes most frequently are represented by various strains of *E. coli*. However, other microbial strains may also be used, such as bacilli (e.g. *Bacillus subtilis*), various species of *Pseudomonas*, or other bacterial strains. In such procaryotic systems plasmid vectors which contain replication sites and control sequences derived from a species compatible with the host are used. For example, *E. coli* is typically transformed using derivatives of pBR322, a plasmid derived from an *E. coli* species by Bolivar et al., *Gene*, 2:95 (1977). Commonly used procaryotic control sequences, which are defined herein to include operons with promoters for transcriptional initiation, optionally with an operator, along with ribosome binding site sequences, include such commonly used promoters as the beta-lactamase (penicillinase) promoter, lactose (lac) promoter systems (*Nature*, 198:1056 (1977), the tryptophan (trp) promoter system (*Nucleic Acids Res.*, 8:4057 (1980), the lambda-derived PL promoter and N-gene ribosome binding site (*Nature*, 292:128 (1981). Any available promoter system compatible with prokaryotes can be used.

The expression systems useful in eucaryotic hosts comprise promoters derived from appropriate eucaryotic genes. A class of promoters useful in yeast, for example, includes promoters for synthesis of glycolytic enzymes, including those for 3-phosphoglycerate kinase (*J. Biol. Chem.*, 255:207 (1980). Other promoters include those from the enolase gene (*J. Biol. Chem.*, 256:1385 (1981) or the Leu2 gene obtained from YEp13 (*Gene*, 8:121 (1978).

Suitable mammalian promoters include metallothionein, the early and late promoters from SV40 (*Nature*, 273:113 (1978), or other viral promoters, such as those derived from polyoma, adenovirus II, bovine papilloma virus or retroviruses. Suitable viral and mammalian enhancers may also be used. In the event plant cells are used as an expression system, the nopaline synthesis promoter is appropriate (*J. Mol. Appl. Gen*, 1:561 (1982).

The expression system is constructed from the foregoing control elements which are operably linked to the CDS sequences by employing standard ligation and restriction techniques which are well understood in the art. Isolated plasmids, DNA sequences, or synthesized oligonucleotide are cleaved, tailored, and religated in the forms desired.

Other systems for expression of CDS encoding cDNA include insect cells and vectors suitable for use in these cells. These systems are known in the art, and include, for example, insect expression transfer vectors derived from the baculovirus *Autographa californica* nuclear polyhedrosis virus (AcNPV), which is a helper-independent, viral expression vector. Expression vectors derived form this system use the strong viral polyhedron gene promoter to drive expression of heterologous genes. Currently the most commonly used transfer vector for introducing foreign genes into AcNPV is pAc373. Many other vectors, including, for example, pVL985 know to those of skill in the art, have also been designed for improved expression.

Methods for the introduction of heterologous DNA into the desired site in the baculovirus virus are known in the art. For example, the insertion can be into a gene such as the polyhedron gene, by homologous recombination; insertion can also be into a restriction enzyme site engineered into the desired baculovirus gene. The inserted sequences may be those which encode all or varying segments of the polyprotein.

The signals for posttranslational modifications, such as signal peptide cleavage, proteolytic cleavage, and phosphorylation, appear to be recognized by insect cells. The signals required for secretion and nuclear accumulation also appear to be conserved between the invertebrate cells and vertebrate cells. Examples of the signal sequences from vertebrate cells which are effective in invertebrate cells are known in the art, for example, the human interleukin-2 signal ($1L2_s$) which is a signal for transport out of the cell, is recognized and properly removed in insect cells.

EXAMPLE 6

Preparation of Probes

This example describes preparation of labeled probes for detection of CDS-1.

Several probes coding for various regions of the CDS polypeptide were used to optimize locating regions of high conservation. Avian CDS cDNA was labeled with $\alpha^{32}P$ dCTP and purified by Sephadex G-50 chromatography. Filters were then washed twice at room temperature for 15 minutes in 1 liter 2×SSPE and 0.2% SDS per 40 filters, followed by two 15 minute 50° C. washes in 0.1×SSPE and 0.2% SDS, slightly air-dried, and exposed to Kodak XAR-5 film, with intensifying screens, for 48 hours at −70° C.

Positive clones were selected from the library and plaque purified. Various probes derived from the cDNA were utilized to determine whether or not a complete copy of the gene was contained within the genomic clone. Recombinant phage DNA was then extracted, purified, and subjected to restriction digestion using methods known to those skilled in the art. Southern blots of the restriction fragments were hybridized with CDS cDNA to identify fragments containing the CDS gene. These fragments were then isolated and sequenced. From this information a restriction map was constructed and the introns of the gene were identified.

EXAMPLE 7

Preparation of Antibodies to CDS

This example illustrates two approaches utilized to raise antibodies to CDS. Both approaches can be used to generate either polyclonal or monoclonal antibodies.

In one approach, purified denatured CDS was obtained in quantities up to 75 µg and used to immunize mice using standard protocols. About 25 µg of CDS was adequate for immunization. For screening hybridomas, denatured CDS, which is soluble in 0.1% TFA and acetonitrile, was radioiodinated and used to screen murine B-cell hybridomas for those which produce antibody. This procedure required only small quantities. 20 µg of CDS was sufficient for labeling and screening of several thousand clones.

In the second approach, the amino acid sequence of CDS, as sequenced or deduced from the gene, is analyzed to determine regions of high immunogenicity. The corresponding polypeptides are synthesized and are used in suitable immunization protocols to raise antibodies. Analysis to select appropriate epitopes is described by, for example, Ausubel, F. M. et al (*Current Protocols in Molecular Biology*, John Wiley & Sons, Vol 2, Sec. IV, pp. 11.14.1, (1989)). The optimal selections are usually the C-terminus, the N-terminus and internal regions of the polypeptide which are likely to be exposed to the external environment when the molecule is in its natural conformation (this determination is based on the hydrophilicity of the sites). Typically, selected peptides, about 15 residues in length, are synthesized using an Applied Biosystems Peptide Synthesizer Model 431A using fmoc-chemistry and coupled to keyhole limpet hemocyanin (KLH; Sigma) by reaction with maleimidobenzoyl-N-hydroxysuccinimide ester (MBS). A cysteine is introduced at the N-terminus of the peptide to permit coupling to KLH. Rabbits are immunized with the peptide-KLH complex in complete Freund's adjuvant and the resulting antisera tested for antipeptide activity, for example, by binding the peptide to plastic, blocking with 0.1% BSA, reacting with antisera, washing and reacting with radioiodinated affinity purified specific goat antirabbit IgG.

Hybridomas are prepared and screened using standard techniques. Hybrids are screened using radioiodinated CDS to identify those producing monoclonal antibody. In a typical protocol, prongs of plates (FAST, Becton-Dickinson, Palo Alto, Calif.), are coated with affinity purified specific rabbit-antimouse (or suitable anti species Ig) antibodies at 10 µg/ml. The coated prongs are blocked with 0.1% BSA, washed and exposed to supernatants from hybridomas. After incubation the prongs are exposed to radiolabeled protein, 1 ng/ml. Clones producing antibodies bind a quantity of radioactivity which is detectable above background. Such clones are expanded and subjected to 2 cycles of cloning at 0.3 cell/well. Cloned hybridomas are injected into pristine treated mice to produce ascites, and monoclonal antibody is purified from the ascitic fluid by affinity chromatography on protein A.

EXAMPLE 8

Purification of the 16 kD and 2 DkD CDS-1 Sequence

CDS-1 (Cell Density Signal molecule—1) has been purified to one band on SDS PAGE.

This band was identified by the following criteria. The intensity of this band correlated with biological activity; the band's intensity increased with purification; the band reproducibly showed up in the purified active fractions. Two other identified candidate bands, meeting some but not all of the above criteria, were shown to be known contaminants by sequencing the protein.

The purification consisted of starting with >300 liters of conditioned medium obtained by gently shaking primary cultures of avian tendon cells. This procedure was slightly modified from what was described in the original application. The flasks used were larger (225 $cm^2$) which required more medium (15 ml), the shaking was at a higher rpm (100), and the medium was collected in one hour collections three times on day 4, and five collections on days 5, 6, 7 after isolating the tendon cells from 16 day chick embryos. The collected medium was stored at 4° C. and treated in 60 liter batches through the first column. In each batch the medium was concentrated by ultrafiltration through a 10 kD ultrafilter. Almost all the activity was in the retentate. This was applied to the first column.

Activity from a fraction was measured by taking a small aliquot and adding it to the medium of primary cultures of tendon cells grown as small 6 mM diameter islands in the middle of a 60 mM dish. In control dishes, after the cells in the middle of the island had become confluent the cells on outer edge began to die. Very little activity would prevent the cell death and a small amount of activity would cause the cells at the edge to grow. More activity would increase proliferation in the cells in the middle. And an excess of activity would cause continuous proliferation throughout the island of cells.

The first column used was a wheat germ lectin column. Some of the activity bound (bd) to the column and some of the activity flowed through (ft) the column. Both fractions were saved and purified. separately. The material from 5 batches were combined and applied to the second column. Both the bd and ft active fractions bound to phenyl sepharose column when loaded in high salt. The active material eluted when the salt concentrations was lowered. The active fractions were diafiltered and applied to the third Q column. The bd active fractions were bound by this column and eluted with increasing salt. The ft active fractions were split by this column into three parts. One part bound to the column, one part was weakly bound, and a third activity remained in the flow through. All of these were separately run on a fourth reverse phase column. An aliquot from the active fractions were run on SDS PAGE. For the hd fraction there was a clear band at 20 kD and in ft fractions there was a band at 16 kD. The difference in molecular weight could be explained by the selection on the first column for more heavily glycosylated proteins.

EXAMPLE 9

Sequencing of Human CDS

This example describes the procedure used for sequencing the human CDS protein herein identified as human equivalent of chick CDS protein having sequence identified as SEQ ID NO:1.

The human CDS sequence is prepared by modified procedures of Examples 1 through 8. The fragment of the chick cDNA is hybridized at low hybridization stringency to select clones from human genomic libraries, the human equivalent of chick cDNA is pulled out, and sequenced.

What is claimed is:

1. An isolated polypeptide depicted by an amino acid sequence Glu-Pro-Leu-Ala-Val-Val-Asp-Leu-Thr-Glu-Lys-Thr-Ile-Ser, set forth in SEQ ID NO: 1.

2. A functionally homologous isolated and purified polypeptide comprising an N-terminal amino acid sequence Glu-Pro-Leu-Ala-Val-Val-Asp-Leu-Thr-Glu-Lys-Thr-Ile-Ser, set forth in sequence (SEQ ID NO: 1)
   wherein said amino acid sequence is a N-terminal portion of a cell density signal protein which stimulates a procollagen expression, proliferation and differentiation of connective tissue and tendon and ligament cells.

3. A purified cell density signal protein isolated from an avian fibroblasts which stimulates a procollagen expression and proliferation and differentiation of connective tissue and tendon and ligament cells comprising an N-terminal amino acid sequence Glu-Pro-Leu-Ala-Val-Val-Asp-Leu-Thr-Glu-Lys-Thr-Ile-Ser, set forth as SEQ ID NO: 1; and
   wherein said protein stimulates said procollagen expression and proliferation and differentiation of connective tissue and tendon and ligament cells as a native cell density signal protein isolated from fibroblast cells.

4. The protein of claim 3 of an apparent molecular weight of at least about 16 kD to about 35 kD when analyzed on SDS polyacrylamide gel electrophoresis (SDS-PAGE),
   said protein being stable at pH from 5.2 to pH 8, with retention of at least 75% of stimulation of the procollagen expression and proliferation and differentiation of connective tissue and tendon and ligament cells;
   said protein being sensitive to inactivation to less than 40% of original activity by Tris ion;
   said protein being resistant to inactivation by trypsin;
   said protein being sensitive to pronase and proteinase K; and
   said protein being further heat and DTT stable with retention of stimulation of the procollagen expression and proliferation and differentiation of connective tissue and tendon and ligament cells greater than 75%.

5. The protein of claim 4 of an apparent molecular weight of 16 kD.

6. The protein of claim 5 purified to about 95% homogeneity.

7. A recombinant cell density signal protein consisting essentially of a N-terminal amino acid sequence set forth as SEQ ID NO: 1 positioned at the cell density protein's N-terminus,
   wherein said cell density protein possesses a biological activity of a native cell density signal isolated from fibroblast cells.

* * * * *